United States Patent
Wei et al.

(10) Patent No.: US 12,023,399 B2
(45) Date of Patent: Jul. 2, 2024

(54) CLEANSING COMPOSITION WITH PYRROLIDONE CARBOXYLIC ACID

(71) Applicant: The Procter & Gamble Company, Cincinnati, OH (US)

(72) Inventors: Karl Shiqing Wei, Mason, OH (US); Kathleen Pearson, Batavia, OH (US); Sandra Liliana Tan, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 94 days.

(21) Appl. No.: 17/846,440

(22) Filed: Jun. 22, 2022

(65) Prior Publication Data
US 2023/0014524 A1    Jan. 19, 2023

Related U.S. Application Data

(60) Provisional application No. 63/216,836, filed on Jun. 30, 2021.

(51) Int. Cl.
| | | |
|---|---|---|
| *A61K 8/00* | (2006.01) | |
| *A61K 8/04* | (2006.01) | |
| *A61K 8/44* | (2006.01) | |
| *A61K 8/46* | (2006.01) | |
| *A61K 8/49* | (2006.01) | |
| *A61Q 19/10* | (2006.01) | |

(52) U.S. Cl.
CPC ............ *A61K 8/4913* (2013.01); *A61K 8/046* (2013.01); *A61K 8/442* (2013.01); *A61K 8/463* (2013.01); *A61Q 19/10* (2013.01); *A61K 2800/596* (2013.01)

(58) Field of Classification Search
CPC .................................................. A61K 8/4913
See application file for complete search history.

(56) References Cited

U.S. PATENT DOCUMENTS

| | | |
|---|---|---|
| 6,106,851 A | 8/2000 | Beerse et al. |
| 6,413,921 B1 | 7/2002 | Childers et al. |
| 6,436,885 B2 | 8/2002 | Biedermann et al. |
| 7,569,530 B1 | 8/2009 | Pan et al. |
| 9,295,251 B1 | 3/2016 | Dyer et al. |
| 9,409,853 B2 | 8/2016 | Schuch et al. |
| 10,357,442 B2 | 7/2019 | Schelges et al. |
| 10,441,522 B2 | 10/2019 | Schelges et al. |

(Continued)

FOREIGN PATENT DOCUMENTS

| | | |
|---|---|---|
| CN | 107693439 A | 2/2018 |
| CN | 110251611 A | 9/2019 |

(Continued)

OTHER PUBLICATIONS

PCT Search Report and Written Opinion for PCT/US2022/035410 dated Oct. 28, 2022, 12 pages.

(Continued)

*Primary Examiner* — Necholus Ogden, Jr.
(74) *Attorney, Agent, or Firm* — Alexandra S. Anoff

(57) ABSTRACT

A cleansing composition containing pyrrolidone carboxylic acid, sodium lauryl sulfate, and a co-surfactant. The cleansing compositions can help skin maintain its natural barrier against bacteria, can help balance skin's pH, and can help skin retain moisture.

15 Claims, 7 Drawing Sheets

(56) References Cited

U.S. PATENT DOCUMENTS

| | | |
|---|---|---|
| 2003/0235550 A1 | 12/2003 | Pan et al. |
| 2005/0271606 A1 | 12/2005 | Iwasaki et al. |
| 2005/0271711 A1 | 12/2005 | Lynch et al. |
| 2007/0232508 A1* | 10/2007 | Oshimura ............ A61K 8/442 510/130 |
| 2022/0023193 A1 | 1/2022 | Wu et al. |

FOREIGN PATENT DOCUMENTS

| | | |
|---|---|---|
| DE | 112007001469 T5 | 6/2009 |
| EP | 0259249 A2 | 3/1988 |
| WO | 0128552 A2 | 4/2001 |
| WO | WO-0128552 A2 * | 4/2001 ............ A61K 31/28 |
| WO | 0152811 A1 | 7/2001 |
| WO | 0153443 A1 | 7/2001 |
| WO | 02078667 A1 | 10/2002 |
| WO | 2017112567 A1 | 6/2017 |
| WO | 2017132356 A1 | 8/2017 |
| WO | 2020212958 A1 | 10/2020 |

OTHER PUBLICATIONS

All Office Actions; U.S. Patent Application U.S. Appl. No. 18/319,962, filed on May 18, 2023.

Unpublished U.S. Appl. No. 18/319,962, filed on May 18, 2023, Brian Joseph Limberg et al.

* cited by examiner

CLEANSING COMPOSITION WITH PYRROLIDONE CARBOXYLIC ACID

FIELD OF THE INVENTION

This application relates to cleansing compositions, in particular foaming hand wash, liquid hand wash, and body wash compositions, with surfactant and pyrrolidone carboxylic acid, and methods relating thereto.

BACKGROUND OF THE INVENTION

Washing with a cleansing product, such as hand wash or body wash, and water can remove dirt and germs from skin. Skin provides the first line of defense against bacteria. Healthy skin contains natural moisturizing factors (NMF). In addition to helping skin retain moisture, NMF can also act as a buffer that can help skin retain its acid mantle. The acid mantle is a very fine, slightly acidic film on the skin that acts as a barrier to bacteria. Cleansing products can wash away the NMF. When NMF is lost, our acid mantle is disrupted and the skin barrier is weakened, which can lead to dry cracked skin and can compromise skin's ability to protect against bacteria.

Therefore, there is a need for a cleansing product that effectively removes bacteria from the skin surface, while also balancing skin pH to maintain skin's acid mantle and its ability to defend against bacteria.

SUMMARY OF THE INVENTION

A cleansing composition comprising: (a) about 0.005% to about 0.1% pyrrolidone carboxylic acid; (b) about 2% to about 7% sodium lauryl sulfate; (c) about 0.5% to about 5% of a co-surfactant selected from zwitterionic surfactant, amphoteric surfactant, nonionic surfactant, or combinations thereof; wherein the composition comprises a pH of about 3 to about 6.

A liquid hand wash composition comprising: (a) about 5% to about 5.5% sodium lauryl sulfate; (b) about 2% to about 2.5% cocamidopropyl betaine; (c) about 0.025% to about 0.035% pyrrolidone carboxylic acid; wherein the composition comprises a pH of about 4 to about 5 and a viscosity of about 5000 cps to about 10,000 cps.

A foaming liquid hand wash composition comprising: (a) about 3% to about 4% sodium lauryl sulfate; (b) about 1% to about 2% cocamidopropyl betaine; (c) about 0.025% to about 0.035% pyrrolidone carboxylic acid; wherein the composition comprises a pH of about 4 to about 5.

DETAILED DESCRIPTION OF THE INVENTION

It was found that a cleansing product that can contain an anionic surfactant and pyrrolidone carboxylic acid (PCA) can effectively remove bacteria from the skin surface and can also help balance skin pH to maintain skin's acid mantle and its ability to defend against bacteria.

PCA is a key NMF that is naturally produced in the skin. It was found that PCA can maintain skin's acidic pH due to its natural buffering capacity, while also being gentle to the skin. It was found that PCA works with the skin's protective layer to balance the skin's pH, maintain the skin's acid mantle, and maintain its ability to defend against bacteria.

In all embodiments of the present disclosure, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated.

Unless otherwise indicated, all measurements are understood to be made at 25° C. and at ambient conditions, where "ambient conditions" means conditions under one atmosphere of pressure and at 50% relative humidity. All such weights as they pertain to listed ingredients are based on the active level and do not include carriers or by-products that may be included in commercially available materials, unless otherwise specified.

As used herein, "cleansing composition" refers to compositions intended for topical application to the skin or hair for cleansing.

As used herein, "free of" refers to no detectable amount of the stated ingredient or thing.

As used herein, "perfume" refers to a mixture of volatile organic oils having a pleasant aroma wherein the perfume components have individual molecular weights between 75 and 400 Daltons.

As used herein, "rinse-off" means the intended product usage includes application to skin and/or hair followed by rinsing and/or wiping the product from the skin and/or hair within a few seconds to minutes of the application step. The product is generally applied and rinsed in the same usage event, for example, a shower or washing one's hands.

As used herein, "substantially free of" refers to 2% or less, alternatively 1% or less, alternatively 0.5% or less, and alternatively 0.1% or less of a stated ingredient. The terms "sulfate free" and "substantially free of sulfates" means essentially free of sulfate-containing compounds except as otherwise incidentally incorporated as minor components.

The term "sulfated surfactants" means surfactants which contain a sulfate group. The term "substantially free of sulfated surfactants" means essentially free of surfactants containing a sulfate group except as otherwise incidentally incorporated as minor components.

Figure 1:
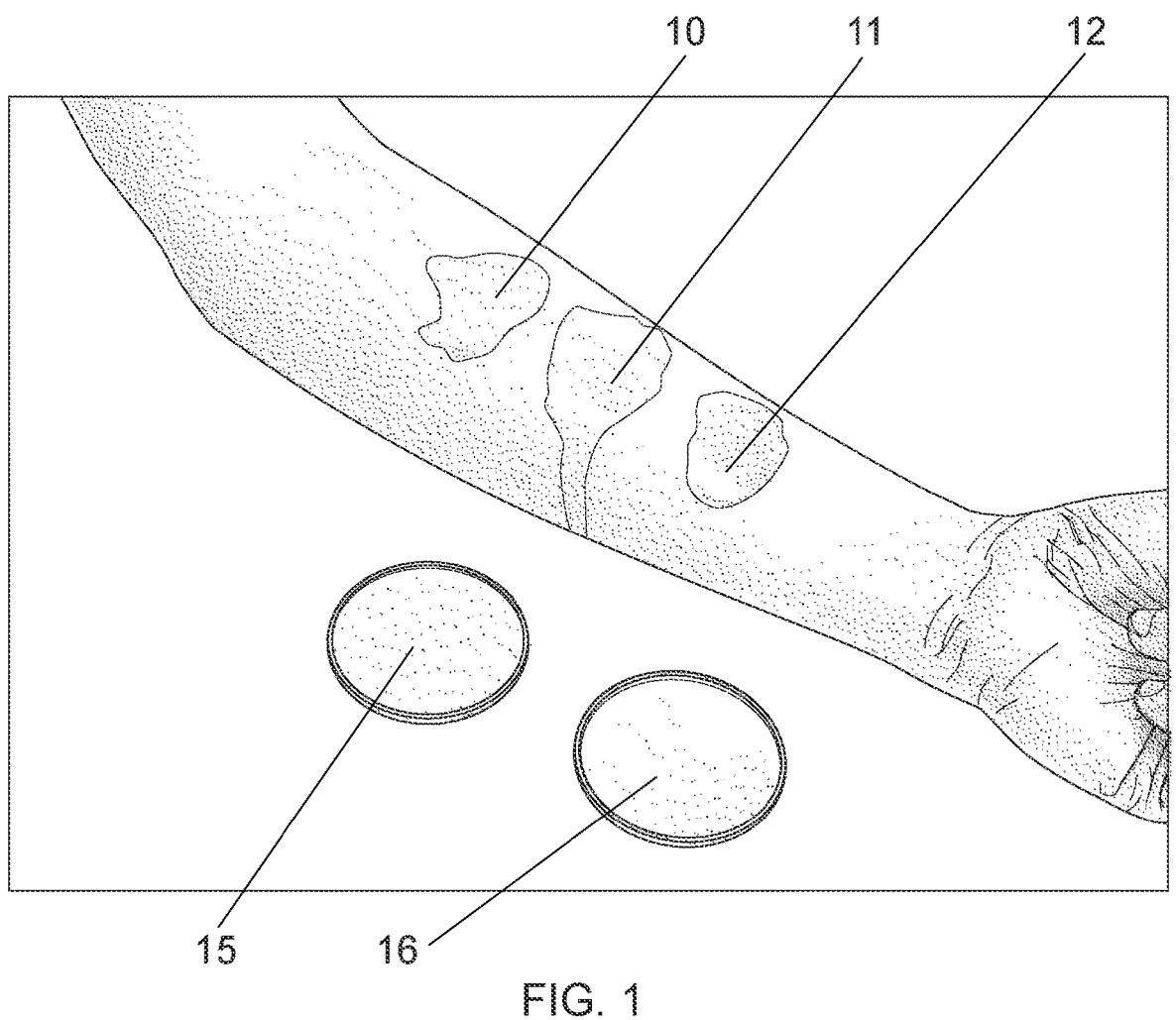
FIG. 1 is an image of an indicator applied to three samples on the arm of a subject.

FIG. 1 shows an indicator that turns yellow (see reference number 15) at pH lower than 5 and turns purple (see reference number 15) when the pH is above 6. When the indicator is applied on skin (see reference number 11), the color of the indicator on skin is yellow, similar to the color of the indicator added to the solution with pH 4-5 (see reference number 15). This shows the skin's acid mantle. The color of the indicator on the inventive cleansing product that includes PCA (see reference number 11), which corresponds to the liquid hand wash formula in Example 1 in Table 5, described herein, is similar to the yellow color of the indicator on skin, indicating that the inventive cleansing product can support skin's acid mantle. Conversely, the commercially available hand wash without PCA turns to a brown color (see reference numeral 12) indicating a higher pH, which may cause disruption to the acid mantle.

It was found that cleansing products that contain PCA can protect the skin's acid mantle even better than water.

Figure 2A:
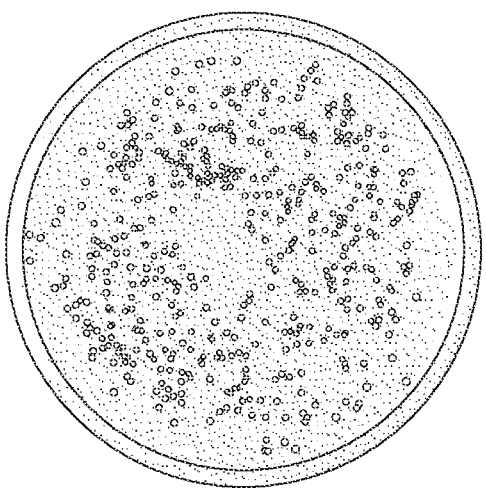
FIG. 2A is an image of a petri dish with pH 5.99 with a culture of *S. aureus* after incubation.
Figure 2B:
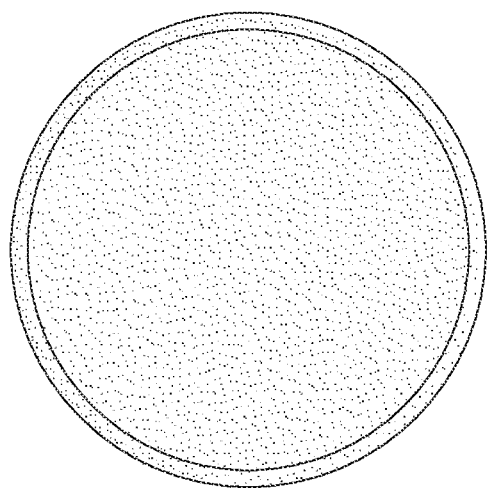
FIG. 2B is an image of a petri dish with 0.03% pyrrolidone carboxylic acid and pH 4.5 with a culture of *S. aureus* after incubation.

The *Staphylococcus aureus* (ATCC #6538) bacteria cultures used herein can be created from commercially available Trypticase Soy Agar (TSA) plates that are streaked and incubated 17-20 hours at 35° C.±2° C. The resulting bacteria are grown in a conventional saline buffer solution with the optical density adjusted to deliver $10^9$ to $10^{10}$ cfu/mL. A sample of the bulk culture can be diluted 1:1,000,000 in saline buffer. 100 ul of the dilute bacteria culture is streak plated onto a TSA plate that is pH adjusted to pH 5.99 or onto a TSA plate that is pH adjusted to pH 4.51 and supplemented with 0.03% PCA. Plates are incubated ~48 hrs at 33° C.±2° C. and photographed for growth as shown in FIGS. 2A (with pH 5.99) and 2B (with pH 4.5 and 0.03% PCA). FIG. 2A shows colonies on the pH 5.99 plate. However, no colonies are observed on the pH 4.51 plates supplemented with 0.03% PCA, as shown in FIG. 2B.

FIG. 3 and

Figure 3:
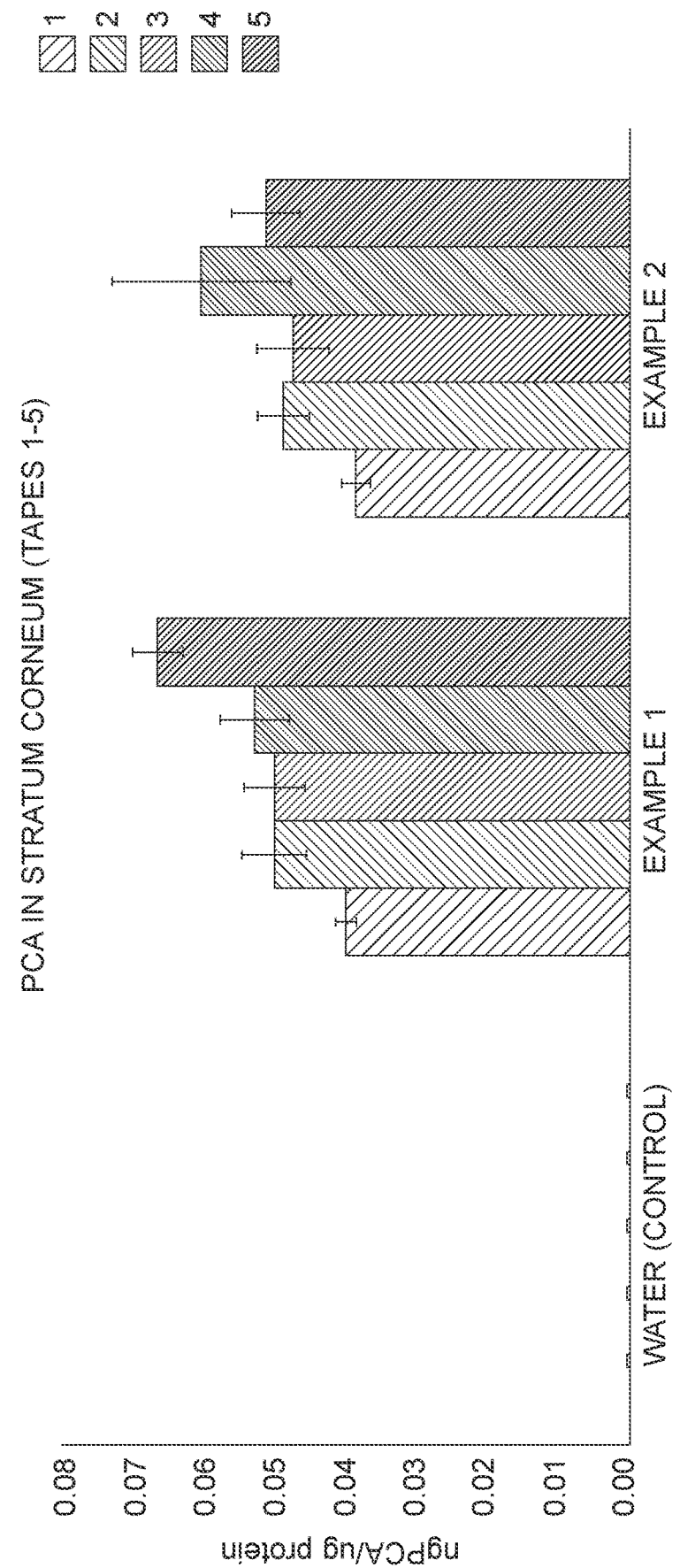
FIG. 3 illustrates the mean amount of pyrrolidone carboxylic acid from an inventive liquid hand wash deposited onto the skin.
Figure 4:
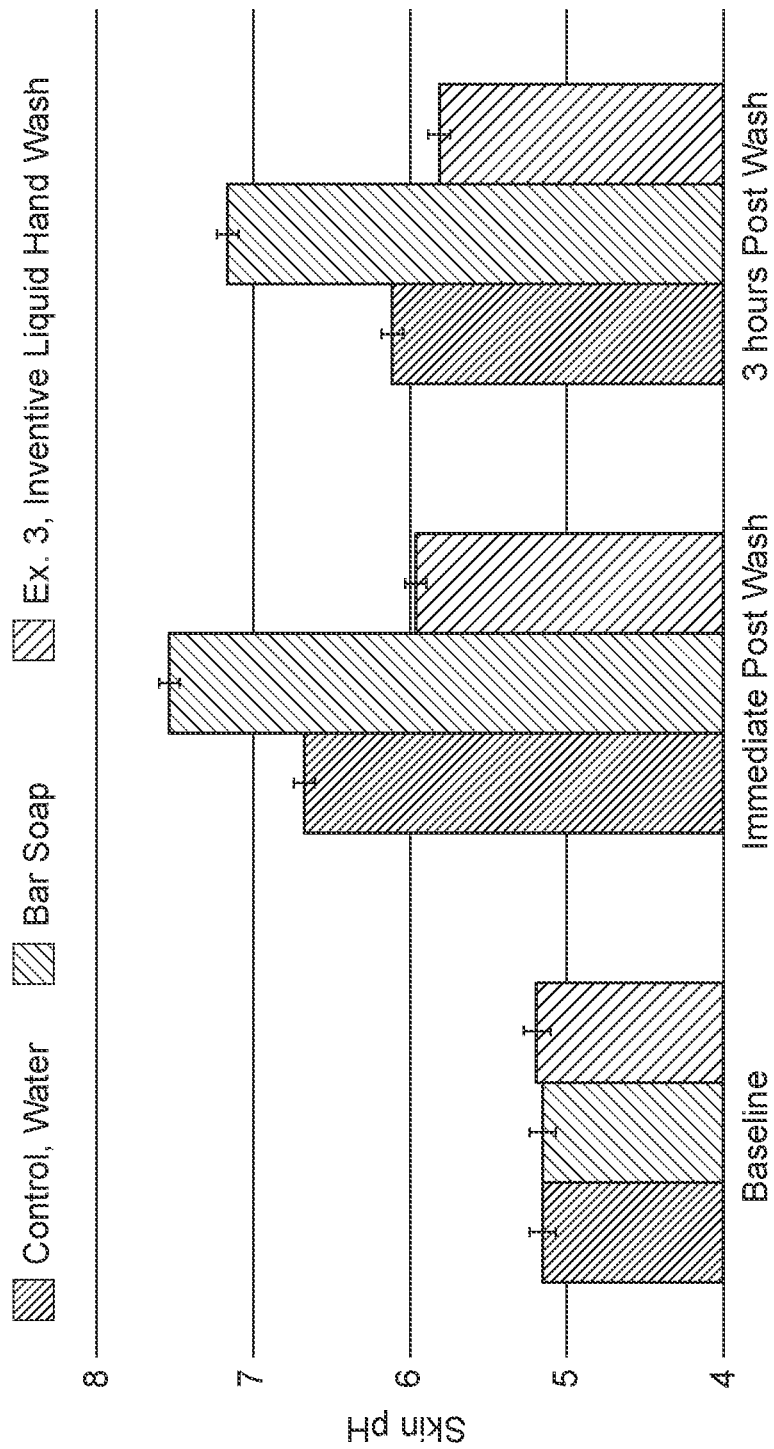
FIG. 4 illustrates pH vs. time for water, bar soap, and an inventive liquid hand wash.

Table 1, below, compares the mean amount of PCA per microgram (μg) of protein from an inventive liquid hand wash (Example 1, Table 5) and an inventive foaming hand wash (Example 2, Table 5) that was deposited onto the skin compared to a control (tap water from Mason, Ohio, USA), as determined by In Vitro Skin Penetration Method. As shown in FIG. 3, PCA was found on each of the five test strips for Examples 1 and Example 2 and there was no PCA on the test strips with the control. This shows that the liquid and foaming hand washes of Examples 1 and 2 deposited PCA on the surface of the skin. It is also believed that PCA also penetrated at least three layers into the skin, which can provide a deep layer of protection to users.

TABLE 1

Results from In vitro Penetration Method

| Strip | Water (Control) (ng PCA/μg protein) | Example 1 (ng PCA/μg protein) | Example 2 (ng PCA/μg protein) |
| --- | --- | --- | --- |
| 1 | 0 | 0.0407 | 0.0393 |
| 2 | 0 | 0.0509 | 0.0497 |
| 3 | 0 | 0.0509 | 0.0483 |
| 4 | 0 | 0.0537 | 0.0615 |
| 5 | 0 | 0.0677 | 0.0522 |

The mean PCA deposition of the hand wash composition can be 0.03 to 0.08 ng PCA/μg protein, alternatively 0.04 to 0.07 ng PCA/μg protein, and alternatively 0.05 to 0.06 ng PCA/μg protein. The mean PCA deposition is determined by In Vitro Skin Penetration Method and calculating the mean for the five test strips.

FIG. 4 and

Table 2, below, compare an inventive liquid hand wash product with PCA (Example 3 in Table 5, described herein) to Irish Spring® Original bar soap (purchased May 2021) and City of Cincinnati water.

The data show that for the 24 people tested, the inventive liquid hand wash product changes the pH less than water and bar soap, immediately after washing and at 3 hours after washing. The change in the pH with the bar soap was greater than 2 on the logarithmic pH scale immediately after washing and at three hours after washing. The change in pH immediately after washing with Example 3 was 0.77 and three hours after wash was 0.62.

TABLE 2

| | Mean pH | | |
| --- | --- | --- | --- |
| | Baseline pH | pH Immediately After Wash | pH 3 Hours After Wash |
| Control, Water | 5.15 | 6.67 | 6.11 |
| Bar Soap | 5.15 | 7.53 | 7.16 |
| Ex. 3, Inventive Liquid Hand Wash | 5.19 | 5.96 | 5.81 |
| Standard Error | 0.083 | 0.066 | 0.069 |

The mean skin pH immediately after washing with the inventive hand wash composition can be 5 to 6, alternatively about 5.2 to less than 6, and alternatively 5.4 to less than 6. The mean change in skin pH immediately after washing with the inventive hand wash composition as compared to baseline can be from 0 to 1.5, alternatively 0.1 to 1.25, alternatively 0.3 to 1, alternatively 0.4 to 0.9, and alternatively 0.5 to 0.8. The mean change in skin pH immediately after washing with the inventive hand wash composition as compared to baseline can be less than 1.5, alternatively less than 1.3, alternatively less than 1.1, alternatively less than 1, alternatively less than 0.9, alternatively less than 0.8. The mean change in skin pH immediately after washing with the inventive hand wash can be less than washing with water and/or bar soap. The skin pH is determined by the In Vivo Skin pH Test Method and the Skin pH Measurement Test Method, described herein.

The mean skin pH 3 hours after washing with the inventive hand wash composition can be 5 to 6.1, alternatively 5.2 to less than 6, alternatively 5.5 to less than 6, and alternatively 5.7 to less than 6. The mean change in skin pH 3 hours after washing with the inventive hand wash composition as compared to baseline can be from 0 to 1, alternatively 0.1 to 0.9, alternatively 0.2 to 0.8, alternatively 0.3 to 0.7, and alternatively 0.4 to 0.65. The mean change in skin pH 3 hours after washing with the inventive hand wash composition as compared to baseline can be less than 0.95, alternatively less than 0.85, alternatively less than 0.8, alternatively less than 0.75, alternatively less than 0.7, and alternatively less than 0.65. The mean change in skin pH 3 hours after washing with the inventive hand wash can be less than washing with water and/or bar soap. The skin pH is determined by the Skin pH Measurement Test Method, described herein.

FIG. 5 and

Figure 5:
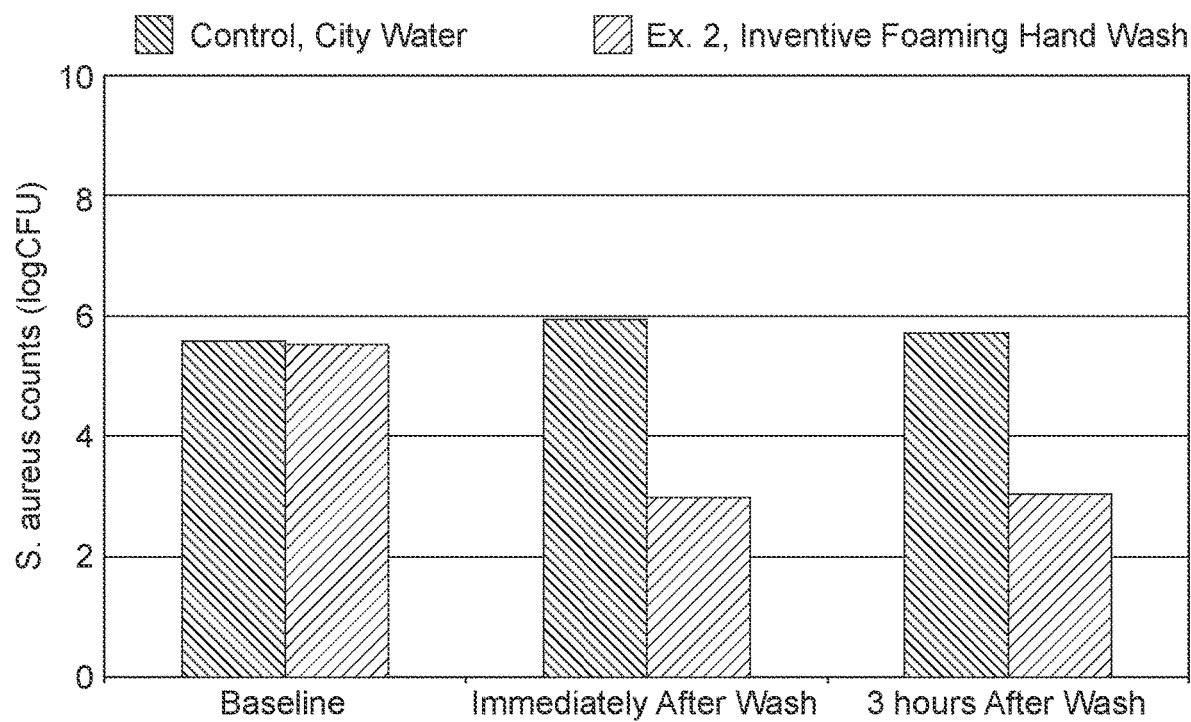
FIG. 5 illustrates *S. aureus* count vs. time for water and an inventive hand wash.

Table 3, below, compares the amount of *S. aureus* bacteria over time for an inventive foaming hand wash product with PCA (corresponding to Example 2 in Table 5, as described herein) to City Water. This test was performed according to the Method for Measuring Residual Antimicrobial Efficacy of a Product, described herein. *S. aureus* is a logarithmic scale, measured in colony-forming unit (CFU). FIG. 5 shows that at the baseline, the samples all had approximately the same concentration of bacteria. However, the foaming liquid hand wash performed much better than City Water immediately after use at time 0 hours and the level of bacteria reduction was the same at three hours.

TABLE 3

S. aureus Concentration

| Timepoint | Product | Mean (logCFU) | Std Dev |
|---|---|---|---|
| Baseline | Control, City Water | 5.59 | 0.72 |
| Baseline | Ex. 2, Inventive Foaming Hand wash | 5.53 | 0.97 |
| Immediately After Wash | Control, City Water | 5.74 | 0.54 |
| Immediately After Wash | Ex. 2, Inventive Foaming Hand wash | 2.98 | 0.48 |
| 3 hours After Wash | Control, City Water | 5.72 | 0.45 |
| 3 hours After Wash | Ex. 2, Inventive Foaming Hand wash | 3.04 | 0.78 |

FIG. 6 and

Figure 6:
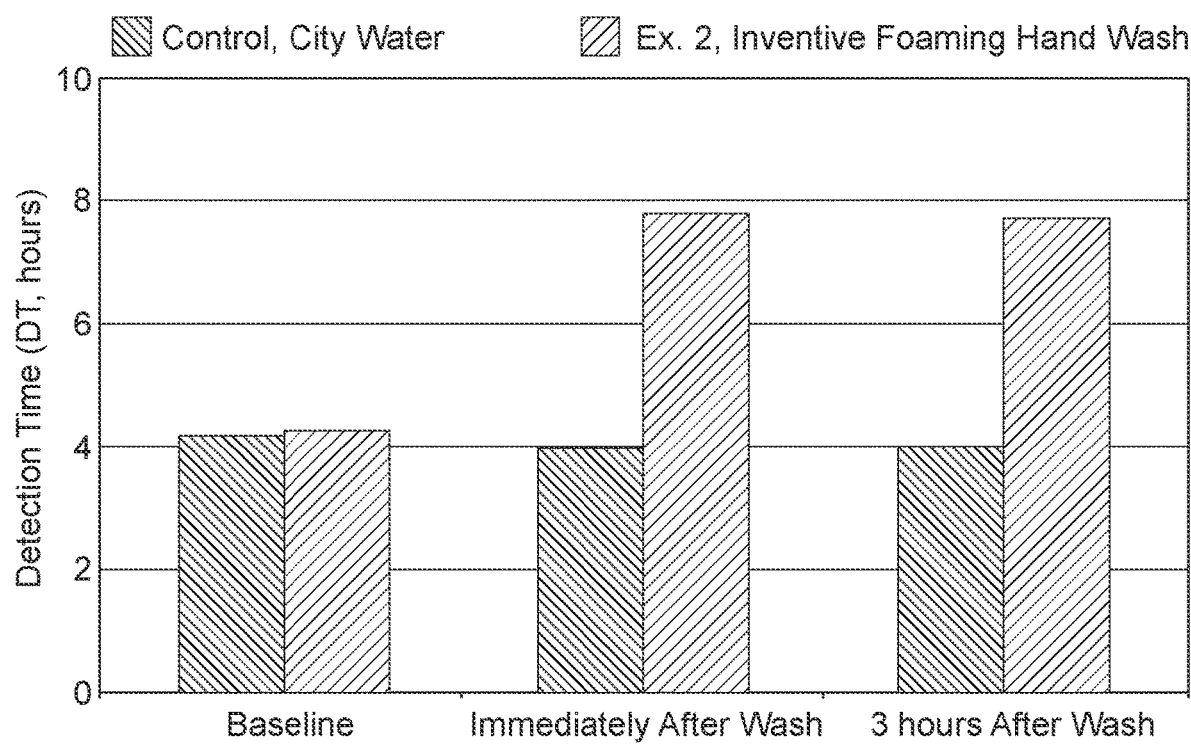
FIG. 6 illustrates mean detection time for water and an inventive foaming hand wash.

Table 4, below, compare the mean detection time (DT) over time for an inventive foaming hand wash product with PCA (corresponding to Example 2 in Table 5, as described herein) to City Water. This test was performed according to the Method for Measuring Residual Antimicrobial Efficacy of a Product with S. aureus, described herein. DT is a logarithmic scale, which corresponds to level of bacteria. FIG. 6 shows that at the baseline, the samples all had approximately the same concentration of bacteria. However, the foaming liquid hand wash performed much better than City Water immediately after use at time 0 hours and the level of bacteria reduction was the same at three hours.

TABLE 4

Mean Detection Time

| Timepoint | Product | Mean (hour) | Std Dev |
|---|---|---|---|
| Baseline | Control, City Water | 4.19 | 1.01 |
| Baseline | Ex. 2, Inventive Foaming Hand wash | 4.28 | 1.35 |
| Immediately After Wash | Control, City Water | 3.99 | 0.75 |
| Immediately After Wash | Ex. 2, Inventive Foaming Hand wash | 7.81 | 0.66 |
| 3 hours After Wash | Control, City Water | 4.01 | 0.62 |
| 3 hours After Wash | Ex. 2, Inventive Foaming Hand wash | 7.72 | 1.08 |

The cleansing composition can have a pH of 2 to 8, alternatively 3 to 6, alternatively 4 to 5, and alternatively 4.5 to 5. pH is measured according to the Product pH Measurement Test Method, described hereafter.

The cleansing composition can leave a person's skin with a mean pH increase that is less than 1, alternatively less than 0.5, alternatively less than 0.25 pH units as compared to a control with water immediately after washing (t=0) and three hours after washing, according to the Method for Skin pH Measurement Test Method, described herein. In some examples, the cleansing composition can decrease the skin's pH by 0.25 or more, alternatively 0.5 or more, alternatively 0.75 or more, alternatively 1 or more as compared to a control with water immediately after washing (t=0) and three hours after washing, according to the In vivo Skin pH Test Method and the Skin pH Measurement Test Method, described herein.

The cleansing composition can have a mean detection time (DT) of greater than 5, alternatively greater than 6, alternatively greater than 6.5, alternatively greater than 7, alternatively greater than 7.5 immediately after washing (t=0) and at three hours (t=3) after washing according to the Method for Measuring Residual Antimicrobial Efficacy of a Product, described herein.

As shown in Table 6, hereafter, it was also found that if PCA was included at 0.110%, the viscosity was significantly reduced and the product may not be consumer acceptable. The composition can have 0.005% to 0.1% PCA, alternatively 0.01% to 0.09%, alternatively 0.015% to 0.08%, alternatively 0.02% to 0.07%, and alternatively 0.025% to 0.05% PCA.

The composition can have a viscosity of 2750 cps to 15,000 cps, alternatively 3000 cps to 13,000 cps, alternatively 4000 cps to 11,000 cps, alternatively 5000 cps to 10,000 cps, and alternatively 6000 cps to 9000 cps, according to the Cone/Plate Viscosity Measurement, described herein.

Surfactant

A rinse-off cleansing composition can include surfactant. Surfactants can provide a cleaning benefit, lather properties, and rheology properties to the compositions. The surfactant may be a single surfactant or a combination of multiple surfactants. In addition, a surfactant may be branched, linear, or a combination thereof. A composition may comprise 1% to 15%, 2% to 12%, from 3% to 10%, from 4% to 8%, or 5% to 7.5%, by weight of the composition, of surfactant. The previous weight percentages of surfactant in the composition include primary surfactant and any cosurfactant.

The primary surfactant may be anionic. The rinse-off cleansing composition may include 0.5% to 10%, 1% to 8%, 2% to 7%, or 3% to 6%, by weight of the composition, of an anionic surfactant. In another example, the rinse-off cleansing composition can be a foaming hand wash and can contain 1% to 6%, 2% to 5%, or 3% to 4%, by weight of the composition, of an anionic surfactant. In another example, the rinse-off cleansing composition can be a liquid hand wash and can contain 2% to 8%, 3% to 7%, or 4% to 6%, by weight of the composition, of an anionic surfactant.

The anionic surfactant can contain any counter ion such as sodium, potassium, ammonium, triethanolamine, etc. The hydrocarbon chain can be an olefin or be branched or linear or cyclic, such as alkyl benzenes, and generally has between 10 and 20 carbons or 12 to 16 carbons. The anionic surfactant can comprise ethylene oxide groups, such as one EO, or two EO, or three EO, e.g., and can be a sulfate, sulfonate or carboxylate, including acidic sulfonates such as sulfosuccinates.

A suitable anionic surfactant can include sodium lauryl sulfate.

Suitable anionic surfactants can include, for example, sodium trideceth sulfate and sodium laureth sulfate. These materials can have varying levels of ethoxylation. Thus, the levels of ethoxylation are represented by an (n), for example, sodium trideceth-n sulfate. n can range 0.5 to 5. Some exemplary anionic surfactants are sodium trideceth-2 sulfate, sodium trideceth-3 sulfate, sodium laureth-1 sulfate, sodium laureth-2 sulfate, sodium laureth-3 sulfate, or combinations thereof.

In some examples, the cleansing composition can be free of or substantially free of surfactants having a sulfate. Suitable surfactants that are substantially free of sulfates can include isethionates, sulfonates, sulfosuccinates, sulfoacetates, acyl glucosides, acyl glycinates, acyl sarcosinare, acyl glutamates, acyl alaninates, glucamide, glucose carboxylates, amphoacetates, taurates, other acyl aminoacids, betaines, sultaines, and/or phosphate esters. Suitable surfactants that are substantially free of sulfates can contain carboxylic acids.

The rinse-off cleansing composition may include 0.25% to 7%, 0.5% to 5%, 1% to 3%, or 1.5% to 2.5%, by weight of the composition, of cosurfactant. The cosurfactant may be, for example, zwitterionic surfactant, amphoteric surfactant, nonionic surfactant, or a combination thereof. Suitable amphoteric or zwitterionic surfactants can include those described in U.S. Pat. Nos. 5,104,646 and 5,106,609. Examples of zwitterionic surfactants can include a betaine, like an alkyl betaine (e.g., coco betaine), alkyl amidopropyl betaine (e.g., cocamidopropyl betaine), and sulfobetaine (e.g., cocamidopropyl hydroxysultaine).

Additional amphoteric detersive surfactants suitable for use in the cleansing compositions can include those surfactants broadly described as derivatives of aliphatic secondary and tertiary amines in which an aliphatic radical can be straight or branched chain and wherein an aliphatic substituent can contain 8 to 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use in the rinse-off cleansing compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain 8 to 18 carbon atoms such that one carbon atom can contain an anionic group, e.g., carboxy, sulfonate, sulfate, phosphate, or phosphonate.

Nonionic surfactants suitable for use can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocamide monoethanolamine, decyl glucoside, or a combination thereof.

Additional surfactants and other ingredients suitable for personal cleansing compositions are found in US Pub. No. 2020/0046623, which is hereby incorporated by reference.

Solubilizers

The cleansing composition can also include solubilizers such as sugar alcohols or glycols. The sugar alcohols can include sorbitol. The glycols can include propylene glycol, dipropylene glycol, polyethylene glycol, derivatives and combinations thereof. In one example, the cleansing compositions can minimize the amount of solubilizers.

The cleansing composition may include no more than 10%, alternatively no more than 5%, alternatively no more than 3%, alternatively no more than 1%, alternatively greater than 0% but less than 3%, or greater than 0% but less than 1%, by total weight of the composition, of a solubilizer.

The cleansing composition can be substantially free of solubilizers, alternatively the composition is free of solubilizers.

pH Adjusting Agents

A variety of compounds may be used to adjust the pH value of a composition. Such suitable compounds can include, but are not limited to, citric acid, lactic acid, salicylic acid, succinic acid, hydrochloric acid, sodium hydroxide, magnesium hydroxide, triethanol amine, diethanol amine, ethanol amine, monoethanol amine, and any combinations thereof. In some examples, the pH adjusting agent can be citric acid. The pH adjusting agent may comprise greater than 0 wt % to 2% of the total weight of the composition.

Optional Ingredients

A variety of optional ingredients can also be added to a cleansing composition. Such suitable ingredients can include, but are not limited to, structurants, humectants, fatty acids, inorganic salts, antimicrobial agents, or other actives.

Structurants

A cleansing composition can also include hydrophilic structurants such as carbohydrate structurants and gums. Some suitable carbohydrate structurants include raw starch (corn, rice, potato, wheat, and the like) and pregelatinized starch. Some suitable gums include carrageenan, guar gum and xanthan gum. A cleansing composition may include 0.1% to 30%, 2% to 25%, or 4% to 20%, by weight of the cleansing composition, of a carbohydrate structurant.

Humectants

A cleansing composition can include one or more humectants. Examples of humectants can include polyhydric alcohols. Further, humectants such as glycerin can be included the cleansing composition as a result of production or as an additional ingredient. For example, glycerin can be a by-product after saponification of the cleansing composition. Including additional humectant can result in a number of benefits such as improvement in hardness of the cleansing composition, decreased water activity of the cleansing composition, and reduction of a weight loss rate of the cleansing composition over time due to water evaporation. The humectants may comprise from greater than 0 wt % to 10% of the total weight of the composition.

Inorganic Salts

A cleansing composition can include inorganic salts. Inorganic salts can help to maintain a particular water content or level of the composition and improve hardness of the composition. The inorganic salts can also help to bind the water in the composition to prevent water loss by evaporation or other means. A cleansing composition can optionally include 0.01% to 15%, 1% to 12%, or 2.5% to 10.5%, by weight of the composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

Organic Acids

In addition or instead of PCA, the composition can include an organic acid, in particular an organic acid with a pKa similar to PCA. Suitable organic acids for incorporation into the present compositions can be characterized by a pKa of greater than 3.0. Without wishing to be bound by theory, the pKa selection limitation of the organic acids can serve the fundamental goal of ensuring that at least 50% of the organic acids incorporated into the present compositions remain undisassociated at the desired pH of 3.0 to 4.5.

A cleansing composition can include an organic acid or organic acid mixture. Without wishing to be bound by theory, the organic acids can protonate the carboxylate functionalities on the phospholipid membrane of bacteria and reduce the tendency of the membrane to electronically repel anionic surfactants, thereby facilitating proper interaction between the present, anionic surfactants and the membrane. Moreover, the organic acids disclosed herein facilitate the creation of a low pH buffer on the surface of a substrate, thereby prolonging the residual antimicrobial activity of the compositions and products in which they are incorporated.

The present organic acids can be added directly to the compositions in acidic form or are formed by adding the conjugate base of the desired acid and an amount of a separate acid sufficient to form the undisassociated acid from the base.

Suitable organic acids, in addition or instead of PCA, can include, but certainly are not limited to: adipic acid, gluconic acid, glyconolactone acid, glutamic acid, glycolic acid, glutaric acid, tartaric acid, ascorbic acid, benzoic acid, salicylic acid, malic acid, succinic acid, lactic acid, and mixtures thereof.

Antibacterial Agents

A cleansing composition can include one or more additional antibacterial agents that can serve to further enhance antimicrobial effectiveness of the cleansing composition. A cleansing composition can include, for example, 0.001% to 2%, 0.01% to 1.5%, or 0.1% to 1%, by weight of the cleansing composition, of additional antibacterial agent(s). Examples of suitable antibacterial agents can include piroctone olamine, carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids.

Skin Benefit Agents

The cleansing composition can include 0.5% to 20% of one or more benefit agents or actives.

Examples of suitable benefit agents can include petrolatum, glyceryl monooleate, mineral oil, natural oils, and mixtures thereof. Additional examples of benefit agents can include water insoluble or hydrophobic benefit agents.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (e.g., C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

Preservatives

A cleansing composition can include one or more preservatives, generally included at less than 2% by total weight of the composition. Such suitable preservatives can include, but are not limited to, benzyl alcohol, kathon, propylene glycol, hydroxy acetophenone, sodium benzoate, disodium ethylenediaminetetraacetic acid (EDTA), parabene, phenoxy ethanol, imidazolidinyl urea, and any combination thereof.

Rinse-Off Cleansing Compositions

Rinse-off cleansing compositions may come in many forms. For example, a cleansing composition may be in a liquid form and could be a body wash, shampoo, conditioning shampoo, moisturizing body wash, shower gel, skin cleanser, cleansing milk, in shower body moisturizer, pet shampoo, shaving preparation, etc. The cleansing composition can be a hand wash or body wash composition, for example a liquid hand wash or a foaming hand wash composition.

The cleansing composition can be water-based. It should be understood that an amount of water can be lost, i.e. evaporated, during a process of making a cleansing composition, or subsequently, with water being absorbed by surrounding packaging (e.g. a cardboard carton), and the like. Thus, a cleansing composition can also include materials that tend to bind the water such that the water can be maintained in the cleansing composition at the desired levels. Examples of such materials can include carbohydrate structurants and humectants such as glycerin. The cleansing composition can include water in the amount of more than 80%, alternatively more than 85%, alternatively more than 88%, by total weight of the composition. However, it will be appreciated that a cleansing composition can be anhydrous.

Methods

In some examples, the cleansing compositions described herein can be intended for use as a hand wash. A user can wash their hands with hand wash as follows:

1. If using liquid hand wash, wet hands with clean, running water (warm or cold), optionally turn off the tap, and apply soap. If using foaming hand wash, rinsing hands before applying the soap is optional.
2. If using liquid hand wash, lather by rubbing palms together with the soap. Lather the backs of hands, between fingers, and under nails. If using foaming hand wash, spread the foam across the palms, back of hands, between fingers, and under nails.
3. It is recommended to scrub hands for at least 20 seconds.
4. Rinse hands well under clean, running water.
5. Dry hands using a clean towel or air dry them.

Washing hands with the cleansing compositions described herein can help skin maintain its natural barrier against bacteria.

The cleansing compositions described herein can wash away 99% of bacteria.

The cleansing composition described herein can be a hydrating hand wash. It can have a fresh clean scent, nourishing aloe scent, ocean breeze scent, notes of citrus, notes of lavender, and/or notes of coconut.

The cleansing compositions described herein can help skin maintain its natural barrier against bacteria.

The cleansing compositions described herein can help maintain skin's protective barrier.

The cleansing compositions described herein can help balance skin's pH and can help retain moisture.

The cleansing compositions described herein can enable the skin to be the first line of defense against bacteria.

The cleansing composition can be readily dispersed by a pump and are freely pourable from any suitable container. In some examples, the cleansing composition can be dispensed as a liquid or a foam from a suitable container by squeezing the container. In other examples, the cleansing composition is dispensed when a user actuates (e.g. pushes down on) the pump. In some examples, the cleansing composition is suitable for dispensing by a pump foamer, which is a non-aerosol way of dispensing the liquid cleansing composition as a foam that generally mixes air in a foaming chamber before discharging the composition.

Test Methods

Cone/Plate Viscosity Measurement

The viscosities of the examples are measured by a Cone/Plate Controlled Stress Brookfield Rheometer R/S Plus, by Brookfield. Engineering Laboratories, Stoughton, MA The cone used (Spindle C-75-1) has a diameter of 75 mm and 1° angle. The viscosity is determined using a steady state flow experiment at constant shear rate of $2\ s^{-1}$ and at temperature of 26.5° C. The sample size is 2.5 ml and the total measurement reading time is 3 minutes.

In Vivo Skin pH

This test was performed over an eight-day, forearm pH study designed to study the impact of hand wash products and bar soap on skin pH immediately after skin wash in 24 female subjects age 18-65 (inclusive). This study included a 7-day pre-treatment phase and 1 day of treatment.

First, qualified subjects were provided with Johnson's® Head-To-Toe® Baby Wash & Shampoo to use as pre-conditioning product during the 7 days prior to the Baseline visit, with no product used on forearms on Day 6 and no shower at all on Day 7. At the Baseline visit, subjects had 2 treatment sites marked on the volar surface of their forearms (i.e. there were 8 subjects in each leg), 1 site per arm. Subjects underwent triplicate baseline pH measurements to assess the baseline pH state of each treatment site according to the Skin pH Measurement Test Method, described hereafter. Subsequently, a washing period followed, using test product on one forearm and control product on the other, at random. During the washing period, the forearms of each subject were washed following standard wash procedure. Subjects then had pH measurements taken immediately after washing and 3-hr post washing, according to the Skin pH Measurement Test Method, described hereafter. After the final post wash pH measurements, subject participation in the study was complete.

Skin pH Measurement

Figure 7:
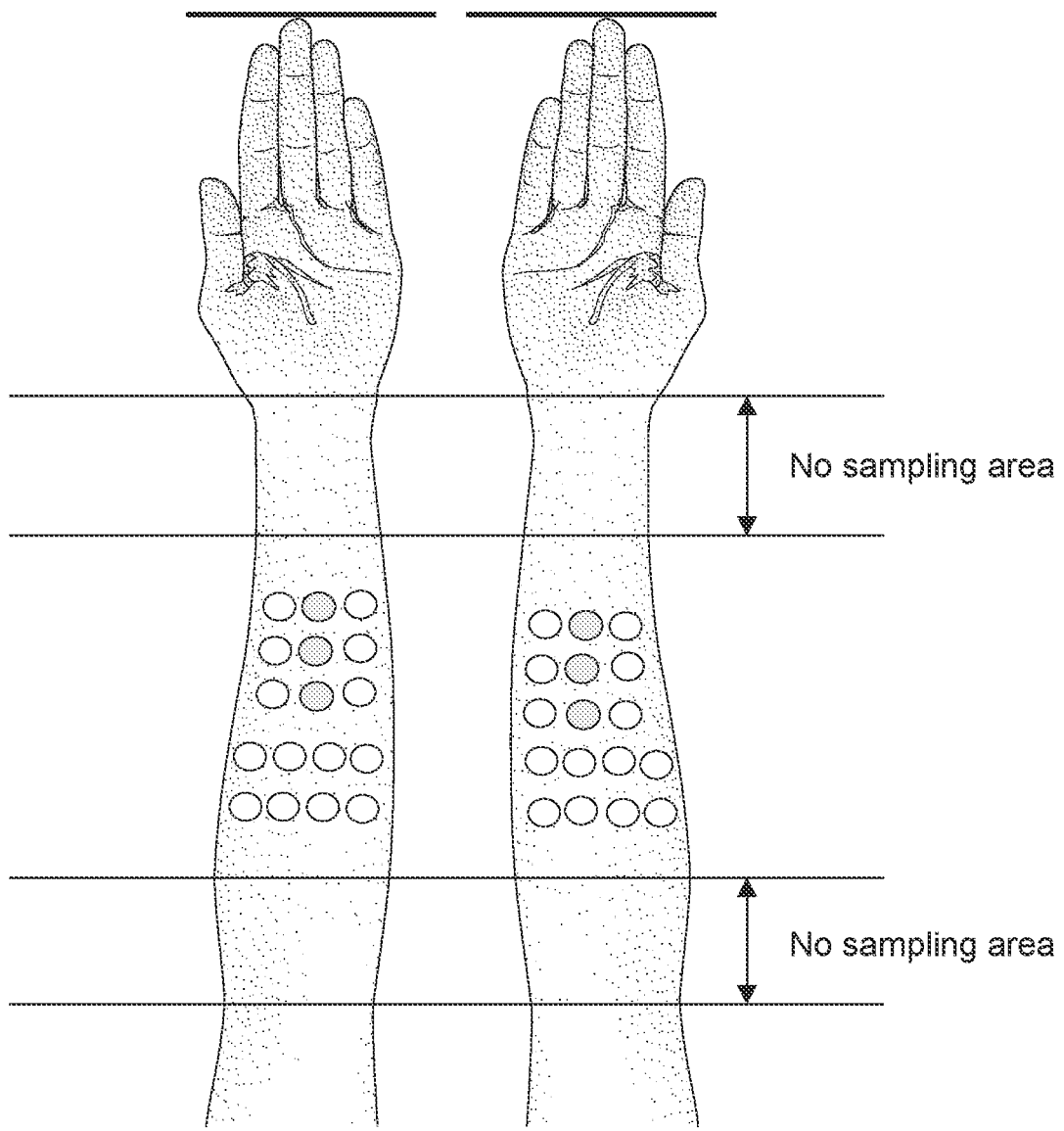
FIG. 7 illustrates where pH readings are taken on the forearm of a test subject.

Measurement Procedure:

Skin pH is assessed using the Hanna® Instruments HI981037 Skin and Scalp pH tester. These non-invasive measurements were taken on each forearm at the sites indicated in FIG. 7.

Measurement Instructions:

Start-Up:
1. Carefully remove the protective cap. Gently wash the end of the probe with distilled water.
2. Store the probe in distilled water between measurements.

Calibration:

The following calibration must be done at the beginning of each study day.
1. Turn on the pH probe with the switch at the top.
2. Press and hold the ON/OFF button until "CAL" is displayed.
3. Open a pH 7.01 solution packet.
4. When "7.01" is displayed, place the tip of the electrode into the packet in the solution.
5. Hold the probe in the solution until the reading stabilizes (approx. 1 min) and the hourglass display disappears.
6. Open a pH 4.01 solution packet.
7. When "4.01" is displayed, place the tip of the electrode into the packet in the solution.
8. Hold the probe in the solution until the reading stabilizes (approx. 1 min) and the hourglass display disappears.
9. "Sto" will be displayed when the calibration is saved.
10. Tester will return to measurement mode automatically and the calibration tags will be displayed.
11. Rinse and store the probe in distilled water or storage solution.
12. If an error message "Err" is displayed, the probe should be cleaned. Soak in cleaning solution or distilled water for 20 minutes.
13. When battery level is low, the tag on the LCD will blink, then "Erb" will be displayed and the tester will power off automatically.

Subject Measurement:
1. To take a measurement, remove the probe from the distilled water, leaving the end of the probe damp (shake off excess).
2. Read right arm first and then left arm.
3. Place vertically on the skin area to be measured.
4. Wait for the measurement to stabilize and the hourglass on the display to disappear. After 60 seconds if the reading appears stable and hourglass is still present, record the reading or wait until display remains stable for several seconds.
5. Record the value displayed to one decimal place. (e.g., "5.2"). Enter this value directly into the sponsor's eCRF database.
6. Take 3 measurements per forearm following the diagram in FIG. 7 (the shaded dots indicated measurement locations).
7. Between measurements, re-wet the tip of the probe in distilled water and shake off excess.
8. Wipe tip with an alcohol wipe after all measurements are completed on one subject.
9. Return probe to the distilled water until ready for next subject.

Shut Down:
1. At the end of the day, turn off the pH meter.
2. Place a small amount of storage solution in the end cap.
3. Gently place the cap back on the pH probe and return to the case In Vitro Skin Penetration Method The skin penetration of product ingredients from topically applied formulations was determined using the in vitro Franz diffusion cell assay (1, 2). The method is described in brief herein. Split-thickness human cadaver skin (Community Tissue Services, Dayton OH) was cut skin into appropriately sized sections (approximately 2 cm×2 cm), and mounted in standard Franz-type diffusion cells (0.79 $cm^2$ surface area) and maintained at 37° C. with stirring. Receptor compartments of each diffusion cell was filled with 5 mL phosphate buffered saline, pH 7.4 plus 1% polysorbate-20 and 0.02% sodium azide. Each treatment group had 6 replicates.

Each test product was spiked with 10 μL $^{14}$C-2-Pyrrolidone-5-carboxylic acid (PCA), 10 μCi per 500 mg product; then mixed with a vortex mixer for 15 seconds. Each skin sample was dosed skin by applying 10 μL/cm$^2$ of product to the skin surface using a positive displacement pipette and spreading over the surface of the skin using a glass rod. The product was lathered/rubbing into the skin with the glass rod for 45 seconds. The skin was then rinsed with water by adding 0.5 mL, pipetting up and down three times and repeating 2 more times. The rinse solutions were combined together for a total rinse volume of 1.5 mL. The dose/rinse procedure two additional times for each diffusion cell.

Ten minutes after product application/rinse, receptor solutions were collected, and the surface of each skin sample was wiped two times with Whatman filter paper soaked with water/Tween 20 and once with 100% ethanol/water to remove unabsorbed (residual) product. The skin was dried under ambient conditions for 30 minutes, then 5 tape strips (D-Squame) were taken. The protein concentration on each tape strip was determined using a SquameScan® 850A.

The remaining epidermis was separated from the dermis by dissection using forceps and dissolve the skin sections in 0.5-1 mL Soluene-350 (Perkin Elmer, Boston, MA) at 60° C. overnight.

The amount of PCA in each compartment (rinse, skin surface wipes, tapes, epidermis, dermis and receptor solutions) was quantitated using Ultima Gold [Perkin-Elmer] liquid scintillation cocktail and liquid scintillation counting (Tri-Carb 2910 TR Liquid Scintillation Analyzer, PerkinElmer, Boston, MA). The total penetration value is the sum of the epidermis, dermis and receptor solution values. Express PCA skin penetration as % of dose and ug or ng/cm$^2$.

Measuring Residual Antimicrobial Efficacy of a Product

This protocol provides a non-invasive method for evaluating the residual antimicrobe efficacy of a rinse-off product e.g. liquid hand wash, body wash product, bar soap, etc. against designated bacteria and fungi. The method includes in vivo product application, skin stratum corneum sampling via tape stripping, germ challenge test on skin samples on the tape strip, and germ load quantification via Soleris® Detection time (DT).

The test organism is *S. aureus* (ATCC® 6538/ATCC® 27127). Ideally, the strain is within 5 generations and has a routine identification at a frequency as makes sense for the bacteria and the test.

The test organism is prepared for the study. For *S. aureus* and *E. coli*, if needed, refresh the test organism by streaking on a trypticase soy agar (TSA) plate and growing 18-24 hrs. On the second day, inoculate 1 colony of organism in a 50 ml tube containing 30 ml trypticase soy broth (TSB), and grow at 35±2° C. for 18 hours±15 min. One the test day, dilute the above bacteria culture by 1:10 or other concentrations to new TSB (e.g. 0.5 ml culture to 4.5 ml TSB media). The test organism culture is used within half an hour for inoculating tape strips for all samples tested.

A) Product Treatment and Sampling Protocol

A target demographic is selected for testing, for example healthy individuals ages 20-60 inclusive. At least ten different subjects are tested. The subjects can be instructed to have a wash out period. For example, the wash out period can be to wash with a prescribed soap for days 1-5, shower on day 6 with City Water only, and to refrain from taking a shower on day 7.

After the wash out period, a baseline skin sample may be taken on the target site prior to any product application. Then, the subjects are either instructed on how to do the following steps or a trained professional may do the steps on the subject. Utilizing tap water with a temperature of 35° C.+/−2° C. and a water flow rate of 4.0 L/min+/−0.3 L/min wet the volar surface of the forearm under the running water. For the liquid products tested herein, 0.7 ml of product was dispensed on the test subject's forearm and spread evenly for 15 seconds. Rinse the forearm for 15 seconds by holding the arm under the running water. Do not rub the arm during rinsing. Remove the arm from the running water. Pat the arm dry with a paper towel without rubbing. The site is now ready for skin sampling with an adhesive. The above steps are repeated three times on the same day before sampling.

Once the target site, here the arm, is ready for sampling, after the third wash, a strip of adhesive tape is adhered to the forearm avoiding folds. The skin site of interest can be marked in advance for consistency. To keep uniform pressure and reach optimal adhesive bond, a roller can be used to press the tape onto the skin surface (ex. twice on each site). Then, the tapes were peeled off from the skin and placed on the surface of a TSA agar plate with the skin sample side up. The tape strips can also be inoculated prior to being placed on the TSA agar plate.

B) Prepping and Testing with an Optical Detection Method (Ex. Soleris®)

Inoculate 10 μl of the tested microorganism culture on the skin sample side of each tape strip. Spread evenly over the tape surface, for example, with a sterile inoculation loop or pipette tip. Use one inoculation loop or pipette tip for each tape strip, and discard inoculation loop or pipette tip after use. Allow the inoculum to visually dry on the surface of the tape strip (approximately ~3-5 minutes).

The inoculated test strips can then be prepped for sampling measurement depending on what is intended to be measured. For example, if the inoculated test strips are going to be run through an optical analysis for detection of microbial growth and/or pH, then the inoculated tape strip residing on the TSA agar plate is placed into a humidified incubator at 35° C. and 60%±20% relative humidity until time of collection (e.g. baseline=immediately before washing, t=0 is immediately after washing, t=3 is three hours after washing).

At each sampling time, aseptically transfer each tape into one NF-TVC (non-fermenting total viable count) vial for continuous monitoring for 24 hours to determine the detection times (DTs). Soleris parameters can be set as: Temperature 34° C.; Threshold: 10; Shuteye: 25; Skip 1. The detection time can be converted to the log CFU count by generating a standard calibration curve of DT vs. Log CFU.

Product pH Measurement

First, calibrate the Thermo Scientific Orion 320 pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 7 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 4 buffer and wait until the pH icon stops flashing and press the measure button. Rinse the electrode with distilled water and carefully wipe with a scientific cleaning wipe. Now the pH meter is calibrated and can be used to test the pH of a solution.

EXAMPLES

The hand wash compositions illustrated in the following Examples illustrate specific embodiments of the hand wash compositions described herein but are not intended to be limiting thereof. Other modifications can be undertaken by the skilled artisan without departing from the spirit and scope of this invention.

The hand wash compositions illustrated in the following Examples are prepared by conventional formulation and mixing methods, an example of which is set forth below. All exemplified amounts are listed as weight percent's and exclude minor materials such as diluents, preservatives, color solutions, imagery ingredients, botanicals, and so forth, unless otherwise specified. All percentages are based on weight unless otherwise specified.

TABLE 5

Hand Wash Examples

|  | Ex. 1 (wt. %) | Ex. 2 (wt. %) | Ex. 3 (wt %) |
|---|---|---|---|
| Sodium Lauryl Sulfate[1] | 5.30 | 3.53 | 5.8% |
| Cocamidopropyl Betaine[2] | 2.25 | 1.50 | 2.5% |
| Sodium benzoate | 0.25 | 0.25 | 0.25 |
| Disodium EDTA | 0.10 | 0.10 | 0.10 |
| Hydroxyproplymethylcellulose[3] | 0.05 | — | 0.05 |
| Benzyl Alcohol | 0.30 | — | 0.30 |
| Methylchloroisothiazolinone, Methylisothiazolinone [4] | 0.03 | 0.03 | 0.03 |
| Fragrance | 1.00 | 0.70 | 1.00 |
| PCA[5] | 0.03 | 0.03 | 0.03 |
| Sodium Citrate | 0.59 | — | 0.59 |
| pH (adjust by citric acid) | 4.5 | 4.5 | 4.5 |
| Water | Q.S. | Q.S. | Q.S. |

Examples 1 to 3 are inventive hand washes that can be dispensed in a pump foam dispenser and/or a pump dispenser. Example 1 and 3 were intended for use as a liquid hand wash for use in a pump dispenser and Example 2 was intended for use as a foaming hand wash pump foam dispenser.

Table 6 shows that the level of PCA can directly impact the viscosity and if PCA is included at too high of a level, the viscosity of the hand wash falls, which can make it too thin to be consumer acceptable. Table 6 shows that when the PCA is included from 0.005% to 0.09% the viscosity is from 8021-8465 cps, which can be consumer acceptable. However, when the PCA was included at 0.110%, the viscosity dropped to 2598 cps, which may be too thin to be consumer acceptable.

Suppliers for Examples in
Table 5 to Table 6
1. Available from Procter & Gamble®
2. Available from BASF®
3. METHOCEL™ 40-101, available from Dow® Chemical Company
4. Kathon™ CG[4], available from Rohm & Hass
5. AJIDEW® A100, available from Ajinomoto® Co., Inc.

It will be appreciated that other modifications of the present disclosure are within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified. A level of perfume and/or preservatives may also be included in the following examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any

TABLE 6

PCA Level Study in the Liquid Hand wash

|  | Ex. A (wt. %) | Ex. B (wt. %) | Ex. C (wt. %) | Ex. D (wt. %) | Ex. E (wt. %) | Ex. F (wt. %) | Ex. G (wt. %) | Ex. H (wt. %) |
|---|---|---|---|---|---|---|---|---|
| Sodium Lauryl Sulfate[1] | 5.30 | 5.30 | 5.30 | 5.30 | 5.30 | 5.30 | 5.30 | 5.30 |
| Cocamidopropyl Betaine[2] | 2.25 | 2.25 | 2.25 | 2.25 | 2.25 | 2.25 | 2.25 | 2.25 |
| Sodium benzoate | 0.25 | 0.25 | 0.25 | 0.25 | 0.25 | 0.25 | 0.25 | 0.25 |
| Disodium EDTA | 0.10 | 0.10 | 0.10 | 0.10 | 0.10 | 0.10 | 0.10 | 0.10 |
| Hydroxyproplymethylcellulose[3] | 0.05 | 0.05 | 0.05 | 0.05 | 0.05 | 0.05 | 0.05 | 0.05 |
| Citric Acid | 0.30 | 0.30 | 0.30 | 0.30 | 0.30 | 0.30 | 0.30 | 0.30 |
| Benzyl Alcohol | 0.30 | 0.30 | 0.30 | 0.30 | 0.30 | 0.30 | 0.30 | 0.30 |
| Methylchloroisothiazolinone, Methylisothiazolinone[4] | 0.03 | 0.03 | 0.03 | 0.03 | 0.03 | 0.03 | 0.03 | 0.03 |
| Fragrance | 1.00 | 1.00 | 1.00 | 1.00 | 1.00 | 1.00 | 1.00 | 1.00 |
| PCA[5] | — | 0.005 | 0.010 | 0.030 | 0.050 | 0.070 | 0.090 | 0.110 |
| Sodium Citrate | 0.59 | 0.59 | 0.59 | 0.59 | 0.59 | 0.59 | 0.59 | 0.59 |
| pH | 4.5 | 4.5 | 4.5 | 4.5 | 4.5 | 4.5 | 4.5 | 4.5 |
| Water | Q.S. | Q.S. | Q.S. | Q.S. | Q.S. | Q.S. | Q.S. | Q.S. |
| Product Viscosity (cps) | 8465 | 8439 | 8302 | 8201 | 8098 | 8021 | 8032 | 2598 | combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

What is claimed is:

1. A cleansing composition comprising:
   a. about 0.005% to 0.090 pyrrolidone carboxylic acid;
   b. about 2% to about 7% sodium lauryl sulfate;
   c. about 0.5% to about 5% of a co-surfactant selected from zwitterionic surfactant, amphoteric surfactant, nonionic surfactant, or combinations thereof;
   wherein the composition has a pH of about 3 to about 6 and a viscosity of about 5000 cps to about 10,000 cps;
   wherein the mean skin pH 3 hours after washing is from about 5 to about 6.1;
   wherein the mean PCA deposition of the cleansing composition is from about 0.03 to 0.08 ng PCA/$\mu$g protein.

2. The cleansing composition of claim 1, comprising about 0.02% to about 0.07% pyrrolidone carboxylic acid.

3. The cleansing composition of claim 2, comprising about 0.025% to about 0.05% pyrrolidone carboxylic acid.

4. The cleansing composition of claim 1, wherein the composition comprises about 4% to about 6% sodium lauryl sulfate and wherein the cleansing composition is a liquid hand wash composition.

5. The cleansing composition of claim 1, wherein the composition comprises about 2% to about 5% sodium lauryl sulfate and wherein the cleansing composition is a foaming hand wash composition.

6. The cleansing composition of 1, wherein the composition comprises about 1.5% to about 2.5% co-surfactant.

7. The cleansing composition of 6, wherein the co-surfactant comprises cocamidopropyl betaine.

8. The cleansing composition of claim 1, wherein the pH is about 4 to about 5.

9. A method of washing hands and helping skin maintain its natural barrier against bacteria comprising:
   a. providing a container that contains the cleansing composition of claim 1 and is the configured to dispense the composition;
   b. dispensing the hand wash composition onto a user's hands;
   c. lathering the composition by rubbing the hands together;
   d. spreading the lathered hand wash composition across the surface of the hands; and
   e. rinsing the composition off of the hands, wherein the cleansing composition helps skin maintain its natural barrier against bacteria.

10. The method of claim 9, wherein the container is a pump dispenser or a pump foam dispenser.

11. The method of claim 9, wherein about 99% of bacteria present on the hands prior to washing are washed away.

12. The method of claim 9, wherein washing the hands with the cleansing composition helps balance skin's pH.

13. The method of claim 9, wherein washing the hands with the cleansing composition helps skin retain moisture.

14. The cleansing composition of claim 1, wherein the mean skin pH 3 hours after washing is from about 5.5 to about 6.

15. The cleansing composition of claim 1, wherein the mean PCA deposition of the cleansing composition is from about 0.04 to 0.07 ng PCA/$\mu$g protein.

* * * * *